(12) United States Patent
Kim et al.

(10) Patent No.: US 12,383,423 B2
(45) Date of Patent: Aug. 12, 2025

(54) HEATING PATCH FOR SKIN CARE

(71) Applicant: AMOLIFESCIENCE CO., LTD., Seoul (KR)

(72) Inventors: Ji Young Kim, Seoul (KR); In Yong Seo, Seoul (KR); Seon Ho Jang, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 912 days.

(21) Appl. No.: 17/618,718

(22) PCT Filed: May 14, 2020

(86) PCT No.: PCT/KR2020/006332
§ 371 (c)(1),
(2) Date: Dec. 13, 2021

(87) PCT Pub. No.: WO2020/251177
PCT Pub. Date: Dec. 17, 2020

(65) Prior Publication Data
US 2022/0241107 A1    Aug. 4, 2022

(30) Foreign Application Priority Data
Jun. 14, 2019 (KR) .................. 10-2019-0070408

(51) Int. Cl.
*A61F 7/00* (2006.01)
*A45D 44/00* (2006.01)
*A61F 7/02* (2006.01)

(52) U.S. Cl.
CPC ............ *A61F 7/007* (2013.01); *A45D 44/002* (2013.01); *A45D 2200/155* (2013.01);
(Continued)

(58) Field of Classification Search
CPC .. A61F 7/007; A61F 2007/007; A45D 44/002
See application file for complete search history.

(56) References Cited

U.S. PATENT DOCUMENTS 5,461,202 A   10/1995  Sera et al.
2011/0172750 A1  7/2011  Cassidy et al.
(Continued)

FOREIGN PATENT DOCUMENTS

JP    H10328223 A   12/1998
KR    200428586 Y1  10/2006
(Continued)

OTHER PUBLICATIONS

Machine Translation of KR 10-1978700 (Year: 2019).*
International Search Report issued in PCT/KR2020/006332, dated Aug. 24, 2020, 2 pages.

*Primary Examiner* — Kaitlyn E Smith
(74) *Attorney, Agent, or Firm* — ROTHWELL, FIGG, ERNST & MANBECK, P.C.

(57) ABSTRACT

A heating patch for skin care including a substrate unit; an application electrode unit formed on the substrate unit in a predetermined pattern, and which includes a first electrode and a second electrode to which power supplied from the outside is applied; a heating unit including first and second heating electrodes, which respectively extend a predetermined length from the first and second electrodes so as to face each other at a certain length without being electrically connected, and a plurality of conductive heating materials formed to have predetermined areas in an overlapping part in which the first and second heating electrodes face each other and generate heat while allowing the first and second heating electrodes to communicate with each other during application of power; and a pair of cover members arranged on both surfaces of the substrate unit to prevent external exposure of the applied electrode unit and heating unit.

16 Claims, 5 Drawing Sheets

(52) U.S. Cl.
CPC ............... *A61F 2007/0003* (2013.01); *A61F 2007/0052* (2013.01); *A61F 2007/0071* (2013.01); *A61F 2007/0086* (2013.01); *A61F 2007/0095* (2013.01); *A61F 2007/0203* (2013.01); *A61F 2007/0226* (2013.01); *A61F 2007/0244* (2013.01)

(56) References Cited

U.S. PATENT DOCUMENTS

| | | |
|---|---|---|
| 2017/0135855 A1 | 5/2017 | Stefan et al. |
| 2020/0078212 A1 | 3/2020 | Seo et al. |
| 2021/0106460 A1* | 4/2021 | Fan .......................... A61F 7/00 |

FOREIGN PATENT DOCUMENTS

| | | |
|---|---|---|
| KR | 200479645 Y1 | 2/2016 |
| KR | 101978700 B1 | 5/2019 |

* cited by examiner

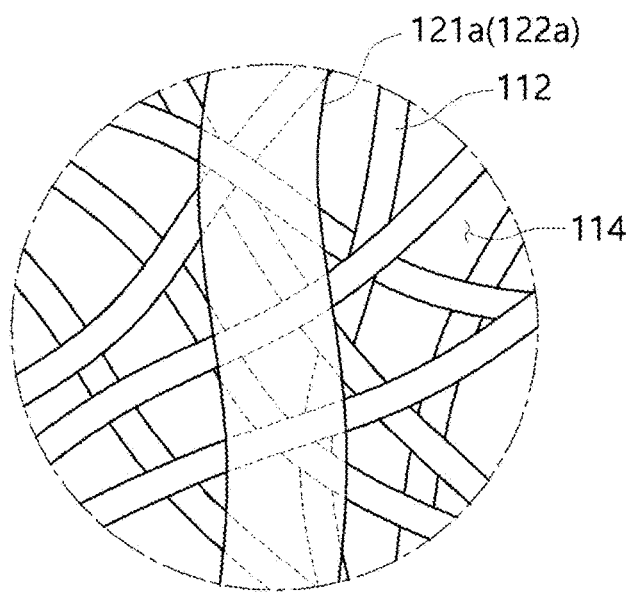
FIG. 5
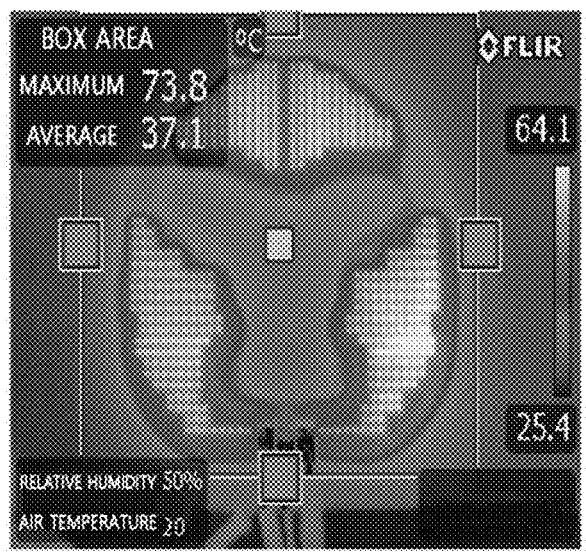
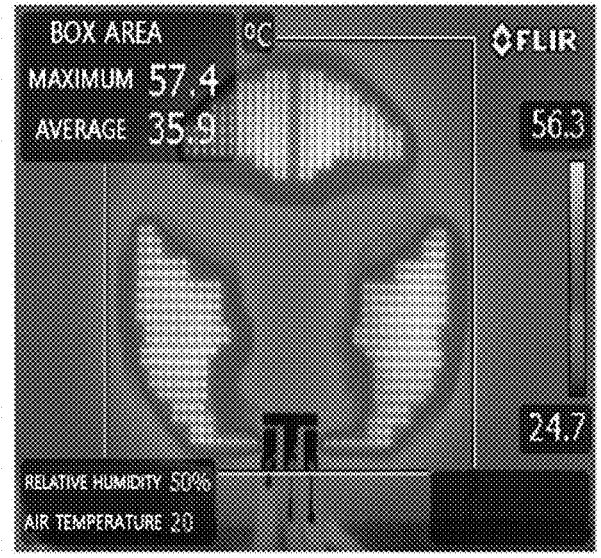
FIG. 6A                    FIG. 6B

HEATING PATCH FOR SKIN CARE

CROSS REFERENCE TO RELATED APPLICATIONS

This application is a 35 U.S.C. 371 National Phase Entry Application from PCT/KR2020/006332 filed May 14, 2020, which designates the United States and claims the benefit of Korean Patent Application No. 10-2019-0070408 filed on Jun. 14, 2019, the disclosures of which are incorporated herein by reference in their entireties.

TECHNICAL FIELD

The present disclosure relates to a heating patch for skin care.

BACKGROUND

Generally, sheet masks are products that contain active materials or cosmetic materials containing various components useful for the skin, such as a moisturizer and a skin lightener, and thus, when attached to skin such as the facial skin, supply nutrients to the skin and improve skin elasticity.

Such sheet masks are made of nonwoven fabric to allow a large amount of active materials or cosmetic materials to be absorbed into the skin. However, there is a problem in that the amount absorbed into the skin and the efficacy of effective components contained in the sheet masks are not satisfactory when using a simple absorption method.

In order to address this problem, conventional sheet masks utilize various methods of improving the composition of effective components or cosmetic materials. However, such methods have problems in that, in terms of cost, a manufacturing cost is increased, and efficiency is decreased relative to the increased cost.

As an alternative, a method of providing heat through a sheet-type heating element has been proposed. However, in the conventional method, since the sheet-type heating element is simply attached to an outer element, there is a problem in that, when applied to a curved area of the body, the sheet-type heating element is not able to be completely adhered to the curved area, and there is a limitation in that the sheet-type heating element simply generates heat and does not generate heat at a uniform temperature.

SUMMARY OF THE INVENTION

The present disclosure is directed to providing a heating patch for skin care that is capable of improving elasticity and flexibility.

The present disclosure is also directed to providing a heating patch for skin care that is capable of implementing a uniform heating temperature.

The present disclosure is also directed to providing a heating patch for skin care that is capable of heating a large area even when a low driving voltage is used.

One aspect of the present disclosure provides a heating patch for skin care, the heating patch including: a substrate part; an application electrode part which is formed in a predetermined pattern on the substrate part and includes a first electrode and a second electrode to which power supplied from the outside is applied; a heating part which includes a first heating electrode and a second heating electrode which extend a predetermined length from the first electrode and the second electrode, respectively, and face each other through certain lengths thereof without being electrically connected to each other and includes a plurality of conductive heating materials which are formed to have a predetermined area in an overlapping portion where the first heating electrode and the second heating electrode face each other and which are configured to, when power is applied, generate heat while causing electricity to flow between the first heating electrode and the second heating electrode; and a pair of cover members disposed on both surfaces of the substrate part to prevent external exposure of the application electrode part and the heating part.

Also, each of the first electrode and the second electrode may be formed of at least two layers including a first pattern formed on the substrate part and a second pattern attached to the first pattern.

Also, the first pattern may be a printed pattern formed by filling pores formed in the substrate part with a conductive paste, and the second pattern may be a metal sheet formed in the same shape as the first pattern.

Also, the second pattern may be attached to one surface of the first pattern via a conductive adhesive layer including a vertical conductive filler.

Also, the first electrode may be formed along an edge of the substrate part, and the second electrode may be formed to be disposed on an inner side of the substrate part.

Also, the first electrode may include a first portion and a second portion which are physically separated from each other so that power applied from the outside is able to be simultaneously applied along two paths, and the first portion and the second portion may be formed on the substrate part so as to be, with respect to a virtual central line, disposed at both left and right sides of the central line.

Also, the heating part may be provided as a plurality of heating parts disposed between the first electrode and the second electrode, and the plurality of heating parts may be connected in parallel to the application electrode part.

Also, the plurality of heating parts may be formed so that a total area of a conductive heating material included in each heating part is the same.

Also, the plurality of heating parts may be formed so that a total length of the first heating electrode and the second heating electrode included in each heating part is the same.

Also, the first electrode and the second electrode may be formed to have a relatively larger width than the first heating electrode and the second heating electrode.

Also, the first heating electrode and the second heating electrode may be a linear pattern bent one or more times.

Also, the conductive heating material may be a conductive constant-temperature heating material.

Also, the cover member may be made of a material that is moisture-proof and flexible.

Also, the cover member may be attached to one surface of the substrate part via an adhesive layer or may be directly fixed to one surface of the substrate part through heat fusion.

Also, the heating patch for skin care may be in the form of a sheet mask that corresponds to the face. In this case, during use, the heating part may be disposed at a position that corresponds to one or more sites among the forehead, cheeks, and chin of the face.

Also, the substrate part may be a porous substrate having flexibility and elasticity.

Advantageous Effects

According to the present disclosure, since a substrate part is formed as a porous substrate having pores and thus secures flexibility and elasticity, a heating patch for skin care can be easily attached even to a curved area such as the face, and adhesion to the skin may be improved.

Also, according to the present disclosure, since a plurality of heating parts can be heated at a uniform temperature, even a large area can be uniformly heated regardless of the position thereof.

Further, according to the present disclosure, since an application electrode is made of two layers, and the plurality of heating parts are connected in parallel to each other, a large area can be easily heated even when a low driving voltage is used.

BRIEF DESCRIPTION OF THE DRAWINGS

FIG. 5 is a view schematically illustrating a method in which the first pattern and the heating electrodes are formed on the substrate part of the heating patch for skin care according to an embodiment of the present disclosure.

FIGS. 6A and 6B show simulation pictures showing heating temperatures according to a configuration of the application electrode part of the heating patch for skin care according to an embodiment of the present disclosure, wherein FIG. 6A shows heating temperatures when the application electrode part is only formed of the first pattern, and FIG. 6B shows heating temperatures when the application electrode part is formed of two layers including the first pattern and a second pattern.

DETAILED DESCRIPTION

Figure 1:
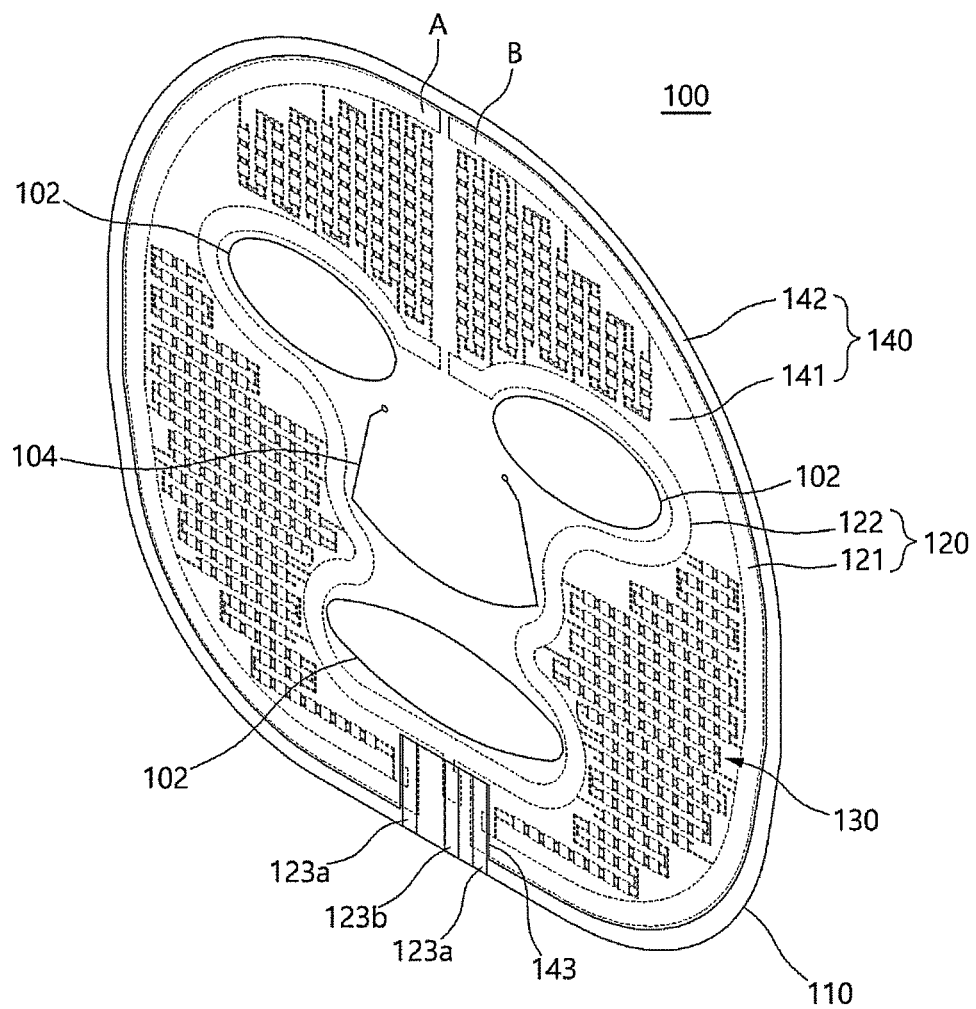
FIG. 1 is a view illustrating a heating patch for skin care according to an s

Hereinafter, embodiments of the present disclosure will be described in detail with reference to the accompanying drawings to allow those of ordinary skill in the art to which the present disclosure pertains to easily practice the present disclosure. The present disclosure may be implemented in various different forms and is not limited to the embodiments described herein. In order to clearly describe the present disclosure, parts unrelated to the description have been omitted from the drawings, and the same or similar elements will be denoted by the same reference numerals throughout the specification.

A heating patch 100 for skin care according to an embodiment of the present disclosure may, in a state of being adhered to the skin of a user, generate heat when power is applied thereto, thus implementing a warming function. In this way, the heating patch 100 for skin care according to an embodiment of the present disclosure may promote penetration of effective components into the user's skin to enhance a skin care effect.

Also, the heating patch 100 for skin care according to an embodiment of the present disclosure may transfer heat to the user's skin to help activate skin collagen and may open pores to induce excretion of unnecessary waste.

Here, the heating patch 100 for skin care according to an embodiment of the present disclosure may be implemented in the form of a sheet mask that is adhered to the entire face and may be implemented so that, even when a warming function is provided to a large area that corresponds to areas of the forehead, cheeks, and chin of the face, a portion being heated is uniformly heated regardless of the position thereof.

In this case, the heating patch 100 for skin care according to an embodiment of the present disclosure may include one or more openings 102 formed to be penetrated, and the openings 102 may be formed at positions that correspond to both eyes and lips of the face when the heating patch 100 for skin care is adhered to the face.

Also, the heating patch 100 for skin care according to an embodiment of the present disclosure may include at least one cut portion 104, and the cut portion 104 may be formed at a position that corresponds to the nose of the face when the heating patch 100 for skin care is adhered to the face.

In this way, since both eyes and lips may be accommodated through the openings 102, one surface of the heating patch 100 for skin care according to an embodiment of the present disclosure may be completely adhered to the face.

As illustrated in FIG. 1, the heating patch 100 for skin care according to an embodiment of the present disclosure includes a substrate part 110, an application electrode part 120, a heating part 130, and a cover member 140.

The substrate part 110 may be formed in the shape of a plate having a predetermined area and may support the application electrode part 120 and the heating part 130 formed on at least one surface thereof.

For example, the substrate part 110 may have substantially the same shape as the cover member 140. In this way, in the heating patch 100 for skin care according to an embodiment of the present disclosure, the heating part 130 may be formed in the form of a sheet having a large heating area through the substrate part 110.

Here, the substrate part 110 may have flexibility and elasticity.

To this end, the substrate part 110 may be formed as a porous substrate having pores, and the application electrode part 120 and the heating part 130 may be formed on at least one surface of the substrate part 110.

In this way, the heating patch 100 for skin care according to an embodiment of the present disclosure may be freely deformable and thus completely adhered even to a curved area such as the face.

Also, in the heating patch 100 for skin care according to an embodiment of the present disclosure, each of the application electrode part 120 and the heating part 130 may be formed by filling the pores with a conductive paste. In this way, even when the substrate part 110 is deformed due to an external force, formation of cracks in a pattern constituting the application electrode part 120 and the heating part 130 may be prevented.

Accordingly, the substrate part 110 may stably serve as a circuit board on which the application electrode part 120 and the heating part 130 are formed as a pattern.

For example, the porous substrate may be a cloth, a fabric, a nonwoven fabric, a porous film, a membrane, or the like in which pores are formed. However, the porous substrate is not limited to the above-listed materials, and any other material may be used without limitations as long as the material has elasticity and flexibility and has pores of a predetermined size formed therein.

Here, pores 114 formed in the substrate part 110 may be formed to have an appropriate pore diameter size in consideration of a particle size of the conductive paste. This is because, in a case in which the pore diameter size of the pores is excessively small, infiltration or impregnation of the particles of the conductive paste may not be facilitated.

As a non-limiting example, as illustrated in FIG. 5, the substrate part 110 may be a nanofiber web in which nanofibers 112 including a synthetic polymer are formed to have the pores 114.

In this way, in a case in which the substrate part 110 is formed as a nanofiber web in the heating patch 100 for skin care according to an embodiment of the present disclosure, the substrate part 110 may have significantly higher bendability as compared to a polyimide film used as a general flexible circuit board and may have an excellent restoration force that allows restoration to its original state even after being folded or wrinkled.

Here, the substrate part 110 may be a monolayer or multi-layer nanofiber web in which a spinning solution, in which a synthetic polymer and a solvent are mixed, is electrospun and formed to have the pores 114. Here, the solvent may be water or alcohol or may also have a form in which, other than water or alcohol, organic solvents such as dimethylacetamide and acetone are used alone or mixed with each other.

Also, the synthetic polymer may be a fiber formation-type polymer that has elasticity and flexibility and is able to implement a nanofiber web through electrospinning.

As a specific example, the synthetic polymer may have a form in which polyvinylidene fluoride (PVDF) is used alone or PVDF and polyurethane (PU) are mixed at a predetermined ratio to secure elasticity and soft touch. As an alternative, the synthetic polymer may also have a form in which PVDF and polyethersulfone (PES) are mixed at a predetermined ratio to secure elasticity and heat resistance.

However, the synthetic polymer is not limited thereto, and any known material may be used as long as the material is a fiber formation-type polymer that is able to implement a nanofiber web through electrospinning and has flexibility and elasticity.

In this way, due to the substrate part 110 being formed as a porous substrate having flexibility and elasticity, the heating patch 100 for skin care according to an embodiment of the present disclosure may secure flexibility and elasticity.

Accordingly, even when attached to a curved area of the skin such as the face, the heating patch 100 for skin care according to an embodiment of the present disclosure may be deformed corresponding to the curved area. Thus, adhesion to the skin may be improved, and heat generated from the heating part 130 may be smoothly transferred to the skin.

Also, in the heating patch 100 for skin care according to an embodiment of the present disclosure, since the pattern constituting the application electrode part 120 and the heating part 130 is configured in a form in which the particles of the conductive paste fill the pores 114 formed in the substrate part 110 as well as the surface of the substrate part 110, the possibility of crack formation may be significantly reduced at the time of deformation due to an external force.

Further, in the heating patch 100 for skin care according to an embodiment of the present disclosure, even when the substrate part 110 is bent or wrinkled and a portion of the pattern constituting the application electrode part 120 and the heating part 130 breaks, at least some portions of the pattern may maintain a connected state through the conductive paste that fills in the pores 114. Thus, the possibility of an occurrence of electrical short circuit may be significantly reduced.

In addition, in the heating patch 100 for skin care according to an embodiment of the present disclosure, since the substrate part 110 is formed as a porous substrate and may have a very small thickness, the overall thickness may be thin. In this way, even when the heating patch 100 for skin care according to an embodiment of the present disclosure is attached to the skin via a material such as a cosmetic material or an ampoule, the possibility that the heating patch 100 for skin care according to an embodiment of the present disclosure is separated from the user's skin may be significantly reduced.

Figure 2:
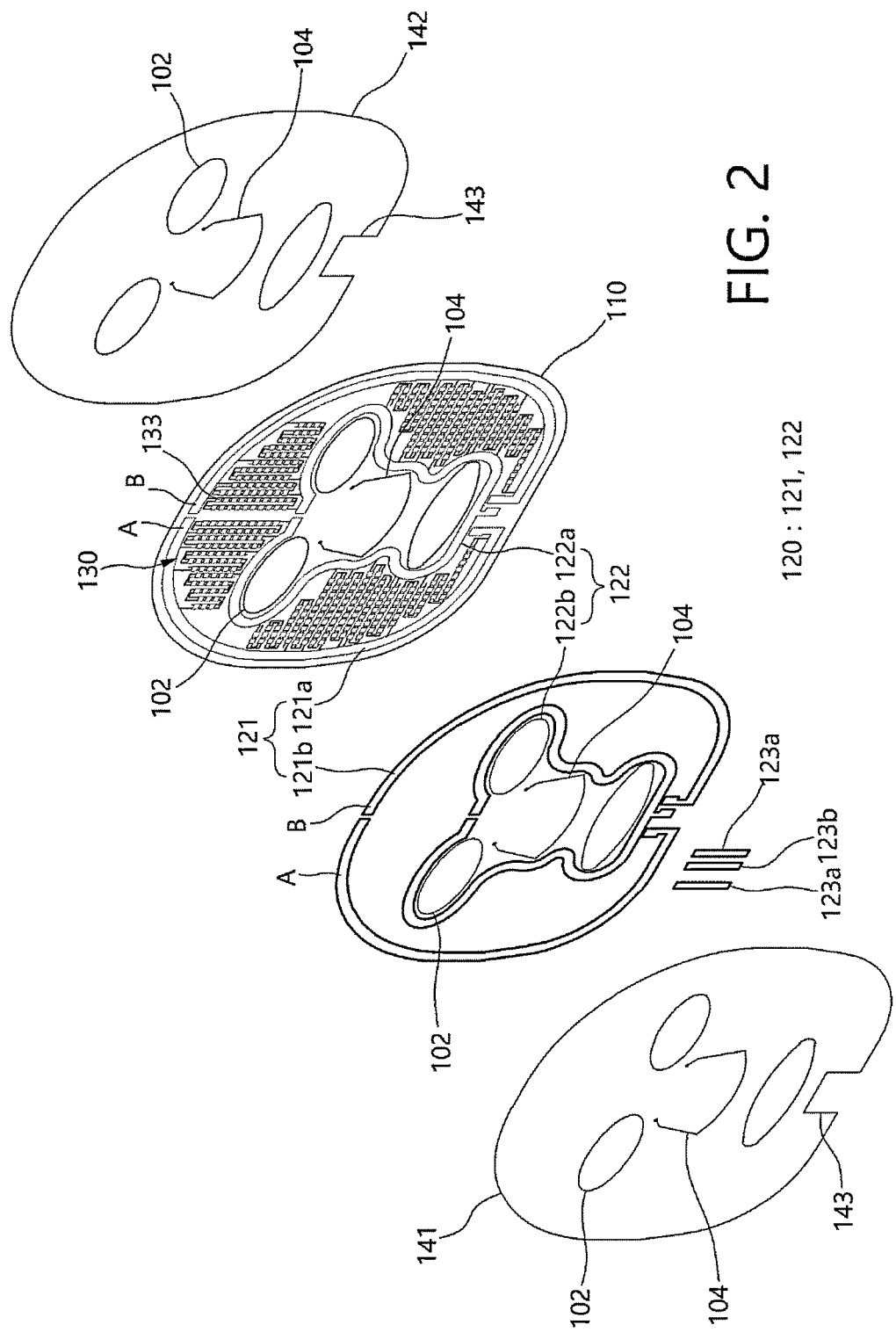
FIG. 2 is an exploded view of FIG. 1.

As illustrated in FIG. 2, the application electrode part 120 may be formed in a predetermined pattern on at least one surface of the substrate part 110 and may, when power is applied thereto, form a path that provides power supplied from the outside toward the heating part 130.

The application electrode part 120 may be formed in a predetermined pattern on one surface of the substrate part 110 as described above and may include a first electrode 121 and a second electrode 122 so that power supplied from the outside may be applied thereto.

That is, the first electrode 121 and the second electrode 122 may be formed on one surface of the substrate part 110 in a state of being spaced apart from each other so that power supplied from the outside may be applied thereto, and when power is applied thereto, current may flow between the first electrode 121 and the second electrode 122 through the heating part 130. In this case, the first electrode 121 may be a positive electrode, and the second electrode 122 may be a negative electrode.

In this way, when power is applied to the application electrode part 120, current may sequentially flow along the first electrode 121, the heating part 130, and the second electrode 122, and power may be supplied toward the heating part 130.

Here, the application electrode part 120 may be formed in the shape of a band to smoothly supply power toward the heating part 130 regardless of the position where the heating part 130 is formed on the substrate part 110.

For example, the first electrode 121 may be formed in the shape of a band along an edge of the substrate part 110, the second electrode 122 may be formed in the shape of a band so as to be disposed on an inner side of the substrate part 110, and the heating part 130 may be formed to be disposed between the first electrode 121 and the second electrode 122.

Also, the application electrode part 120 may be configured to allow power supplied from the outside to be simultaneously supplied through two paths.

For example, the first electrode 121 may include a first portion A and a second portion B which are physically separated from each other, and the first portion A and the second portion B may be formed on the substrate part 110 so as to be, with respect to a virtual central line, disposed at both left and right sides of the central line.

That is, the first portion A and the second portion B of the first electrode 121 may be connected in parallel to the power supplied from the outside.

In this way, as compared to the case in which the first electrode 121 is formed as one body and current flows along the first electrode 121, the heating part 130, and the second electrode 122, a path of current may be shortened when current flows along the first portion A, the heating part 130, and the second electrode 122 or flows along the second portion B, the heating part 130, and the second electrode 122, and resistance of the first portion A itself and resistance of the second portion B itself may be reduced.

Thus, even when a plurality of heating parts 130 are connected in parallel between the first electrode 121 and the second electrode 122, the overall supply time for power to be supplied toward each heating part 130 may be shortened to shorten a reaction time of the heating parts 130, and the size of a driving voltage required to heat the heating parts 130 may be reduced.

Meanwhile, the application electrode part 120 may be formed of at least two layers. That is, the first electrode 121 and the second electrode 122 may respectively include first patterns 121*a* and 122*a* directly formed on the substrate part 110 and second patterns 122*b* and 122*b* stacked on one surface of the first pattern 121*a* and one surface of the first pattern 122*a*, respectively.

Here, as described above, the first patterns 121*a* and 122*a* may be printed patterns formed by filling the pores 114 formed in the substrate part 110 with the conductive paste, and the second patterns 122*b* and 122*b* may be metal sheets formed in the same shape as the first patterns 121*a* and 122*a*.

That is, the first patterns 121*a* and 122*a* may be printed patterns formed on the substrate part 110 by a printing method using the conductive paste, and the conductive paste may completely or partially fill the pores 114 formed in the substrate part 110 as well as the surface of the substrate part 110. Here, the conductive paste may be a Ag paste but is not limited thereto, and any other known conductive paste used to configure an electrode may be applied.

Also, the metal sheet may be a copper foil or an aluminum foil, and the second patterns 122*b* and 122*b* may be attached to one surface of the first pattern 121*a* and one surface of the first pattern 122*a*, respectively, via a conductive adhesive layer.

Here, the conductive adhesive layer may be an adhesive layer including a vertical conductive filler such as Ni, and the second patterns 122*b* and 122*b* may be blanked elements blanked from a metal sheet of a predetermined area to have the same shape as the first patterns 121*a* and 122*a*.

In this way, through the first patterns 121*a* and 122*a*, the application electrode part 120 may be smoothly connected to the heating part 130 formed on the substrate part 110, and through the second patterns 122*b* and 122*b*, the application electrode part 120 may reduce resistance of the first electrode 121 itself and resistance of the second electrode 122 itself. Accordingly, even when the plurality of heating parts 130 are connected in parallel between the first electrode 121 and the second electrode 122, each heating part 130 may be uniformly heated.

This may be confirmed through FIGS. 6A-6B.

That is, as can be seen from FIG. 6A, in a case in which each of the first electrode 121 and the second electrode 122 only includes the first patterns 121*a* and 122*a* and the plurality of heating parts 130 are connected in parallel between the first electrode 121 and the second electrode 122, an average heating temperature of the plurality of heating parts 130 is 37.1° C., and a heating temperature of the heating part 130 that generates heat at the highest temperature among the plurality of heating parts 130 is 73.8° C.

On the other hand, as can be seen from FIG. 6B, in a case in which each of the first electrode 121 and the second electrode 122 is configured in a stacked form including the first patterns 121*a* and 122*a* and the second patterns 122*b* and 122*b* and the plurality of heating parts 130 are connected in parallel between the first electrode 121 and the second electrode 122, an average heating temperature of the plurality of heating parts 130 is 35.9° C., and a heating temperature of the heating part 130 that generates heat at the highest temperature among the plurality of heating parts 130 is 57.4° C.

In this way, it can be seen that a difference in the average heating temperature is not large between the case in which each of the first electrode 121 and the second electrode 122 only includes the first patterns 121*a* and 122*a* and the case in which each of the first electrode 121 and the second electrode 122 is configured in the stacked form including the first patterns 121*a* and 122*a* and the second patterns 122*b* and 122*b*.

However, it can be seen that the heating temperature of the heating part generating heat at the highest temperature in the case in which each of the first electrode 121 and the second electrode 122 only includes the first patterns 121*a* and 122*a* is about 16° C. higher than the heating temperature of the heating part generating heat at the highest temperature in the case in which each of the first electrode 121 and the second electrode 122 is configured in the stacked form including the first patterns 121*a* and 122*a* and the second patterns 122*b* and 122*b*.

In this way, it can be seen that large heating temperature variations occur between the plurality of heating parts 130 connected in parallel between the first electrode 121 and the second electrode 122 in the case in which each of the first electrode 121 and the second electrode 122 only includes the first patterns 121*a* and 122*a*, but, when each of the first electrode 121 and the second electrode 122 is configured in the stacked from including the first patterns 121*a* and 121*b* and the second patterns 122*b* and 122*b*, large heating temperature variations do not occur between the plurality of heating parts 130 connected in parallel between the first electrode 121 and the second electrode 122, and the heating parts 130 may be heated at a uniform temperature.

The heating part 130 may be formed on one surface of the substrate part 110 so as to be electrically connected to the application electrode part 120. The heating part 130 may be heated when power is applied thereto.

Here, the heating part 130 may include a first heating electrode 131 and a second heating electrode 132 which are not electrically connected to each other, and when power is applied, electricity may flow between the first heating electrode 131 and the second heating electrode 132 through a plurality of conductive heating materials 133.

Figure 3:
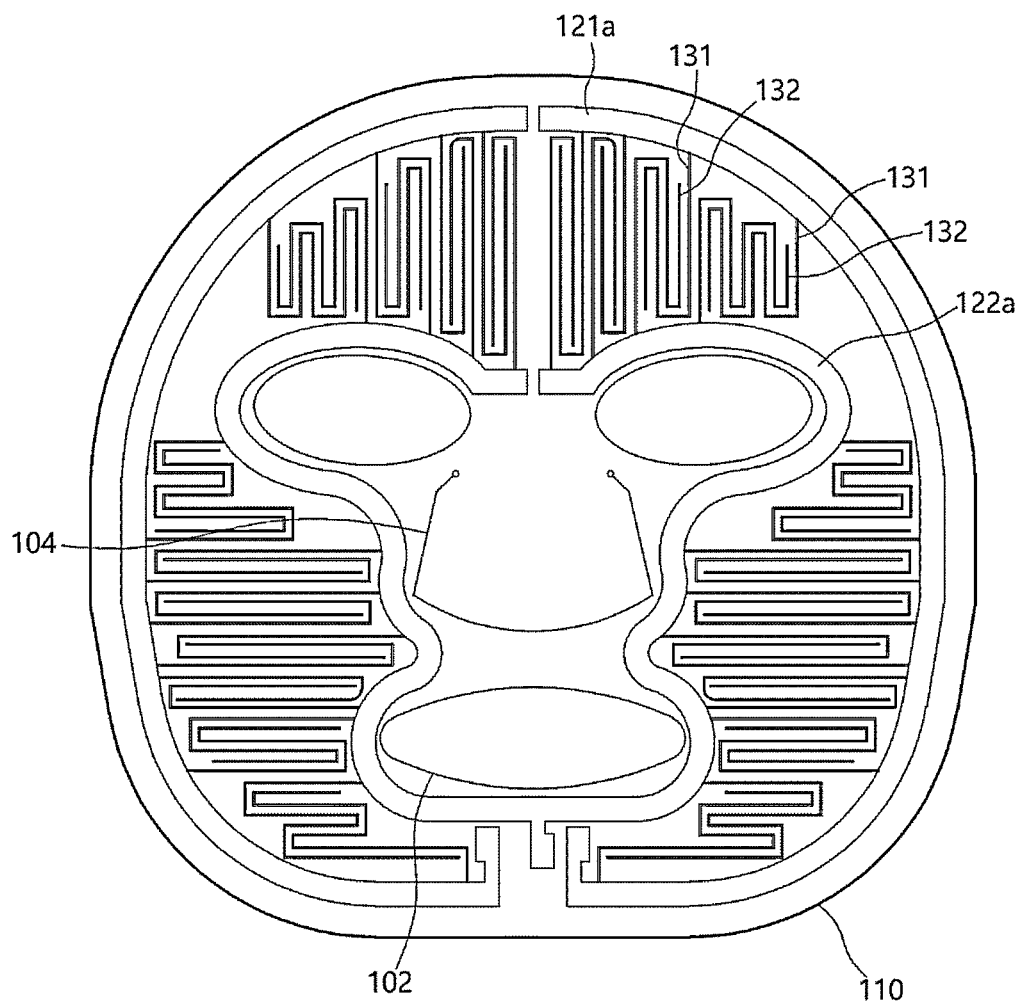
FIG. 3 is a view illustrating a first pattern of an application electrode part and a first heating electrode and a second heating electrode of a heating part which are formed on a substrate part of the heating patch for skin care according to an embodiment of the present disclosure.
Figure 4:
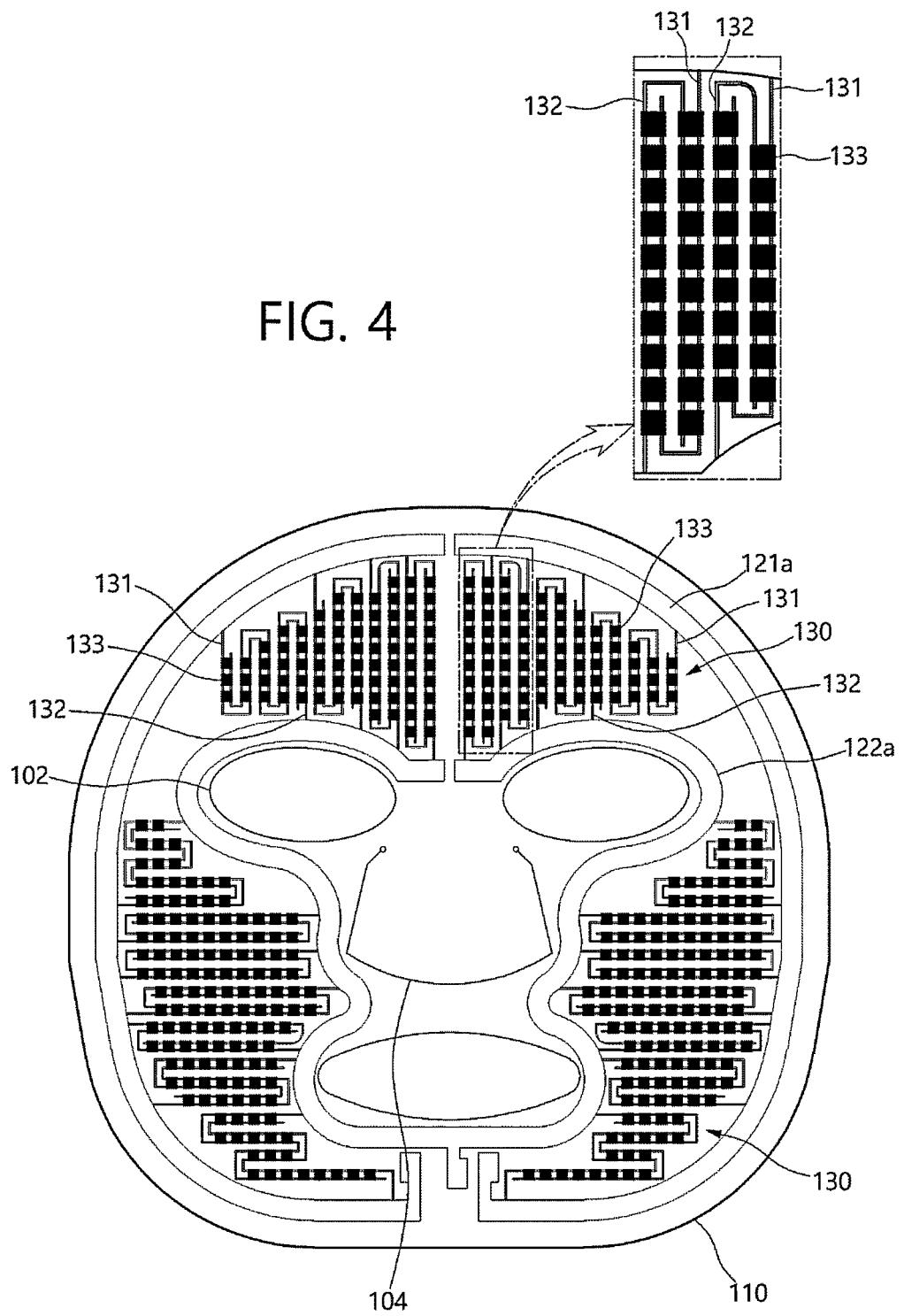
FIG. 4 is a view illustrating a form in which a conductive heating material is formed in FIG. 3.

Specifically, as illustrated in FIGS. 2 to 4, the first heating electrode 131 may be a linear pattern which has a predetermined length and extends from the first electrode 121 toward the second electrode 122, and the second heating electrode 132 may be a linear pattern which has a predetermined length and extends from the second electrode 122 toward the first electrode 121.

In this case, the first heating electrode 131 and the second heating electrode 132 may be formed on the substrate part 110 while being spaced apart at a predetermined gap and facing each other through partial lengths thereof, and the plurality of conductive heating materials 133 may be formed on the substrate part 110 to cover an overlapping portion which is formed through the partial lengths through which the first heating electrode 131 and the second heating electrode 132 face each other.

Accordingly, in a state in which one end portion of the first heating electrode 131 and one end portion of the second heating electrode 132 are connected to the first electrode 121 and the second electrode 122, respectively, the first heating electrode 131 and the second heating electrode 132 may be connected to each other via the plurality of conductive heating materials 133.

In this case, the plurality of conductive heating materials 133 may be formed on the substrate part 110 so as to be spaced apart with a predetermined gap in a longitudinal direction of the first heating electrode 131 and the second heating electrode 132 in the overlapping portion where the first heating electrode 131 and the second heating electrode 132 face each other through the partial lengths thereof.

Here, the plurality of conductive heating materials 133 may serve to, when power is supplied, cause electricity to flow between the first heating electrode 131 and the second heating electrode 132 and generate heat.

Accordingly, when power is supplied toward the heating part 130 through the application electrode part 120, electricity may flow between the first heating electrode 131 and the second heating electrode 132 through the conductive heating materials 133, and the conductive heating materials 133 may generate heat using the supplied power.

In this way, the heating patch 100 for skin care according to an embodiment of the present disclosure may implement a warming function through heat generated from the heating part 130.

Here, each of the first heating electrode 131 and the second heating electrode 132 may be formed as a linear pattern that is bent one or more times. For example, each of the first heating electrode 131 and the second heating electrode 132 may have a shape that is bent one or more times at the center thereof. For example, each of the first heating electrode 131 and the second heating electrode 132 may have any one shape of a " " shape, a " " shape, or a combined shape thereof.

In this way, in the heating patch 100 for skin care according to an embodiment of the present disclosure, even when the plurality of conductive heating materials 133 are spaced apart at a predetermined gap from each other in the longitudinal direction of the first heating electrode 131 and the second heating electrode 132, the heating part 130 may be implemented in the form of a sheet.

Thus, the heating patch 100 for skin care according to an embodiment of the present disclosure may provide heat to a large area of corresponding sites in individual sites such as the forehead, cheeks, and chin of the face.

Meanwhile, the conductive heating material 133 may be made of a conductive constant-temperature heating material to maintain a target temperature when power is supplied.

That is, the conductive constant-temperature heating material may be a material whose resistance increases upon a temperature increase, thus suppressing a heating temperature.

As a non-limiting example, the conductive constant-temperature heating material may be a known positive temperature coefficient (PTC) material, and more specifically, may be a conductive carbon paste.

Accordingly, in the heating part 130, when the heating temperature reaches a target temperature when power is supplied, resistance of the conductive constant-temperature heating material may be increased and a flow of current may be blocked, and thus electrical connection between the first heating electrode 131 and the second heating electrode 132 may be blocked. In this way, the heating part 130 may be prevented from being heated to a temperature higher than the target temperature.

On the other hand, in the heating part 130, when the heating temperature decreases to a temperature lower than the target temperature, resistance of the conductive constant-temperature heating material may be decreased again and a flow of current may be allowed, and thus the first heating electrode 131 and the second heating electrode 132 may be electrically connected to each other. In this way, the heating temperature of the heating part 130 may be increased to the target temperature again through heating.

Thus, in the heating patch 100 for skin care according to an embodiment of the present disclosure, through the above-described process, the heating part 130 may always be heated at a uniform temperature.

In the present disclosure, the heating part 130 may be a printed pattern formed so that the conductive paste fills the pores 114 formed in the substrate part 110.

That is, each of the first heating electrode 131 and the second heating electrode 132 may be a printed pattern formed on the substrate part 110 through a printing method using the conductive paste, and the conductive paste may completely or partially fill the pores 114 formed in the substrate part 110 as well as the surface of the substrate part 110. Here, the conductive paste may be a Ag paste but is not limited thereto, and any other known conductive paste used to configure an electrode may be applied.

Likewise, the conductive heating material 133 may be a printed pattern formed on the substrate part 110 through a printing method, and the conductive heating material 133 may completely or partially fill the pores 114 formed in the substrate part 110 as well as the surface of the substrate part 110.

Meanwhile, in the heating patch 100 for skin care according to an embodiment of the present disclosure, the heating part 130 may be provided as a plurality of heating parts 130. That is, in the heating patch 100 for skin care according to an embodiment of the present disclosure, the plurality of heating parts 130 may be connected in parallel to each other in the longitudinal direction of the application electrode part 120.

In this way, in the heating patch 100 for skin care according to an embodiment of the present disclosure, even when each heating part 130 is formed in the form of a sheet, the overall length of each of the first heating electrode 131 and the second heating electrode 132, which constitute each heating part 130, may be formed to be short. Thus, resistance of the first heating electrode 131 itself and resistance of the second heating electrode 132 itself may be reduced, and the same voltage may be applied to each heating part 130.

Thus, in the heating patch 100 for skin care according to an embodiment of the present disclosure, even when the plurality of heating parts 130 are connected between the first electrode 121 and the second electrode 122, the size of a driving voltage required to heat each heating part 130 at the same target temperature may be reduced.

For example, the plurality of heating parts 130 may be connected in parallel to the application electrode part 120 so as to be disposed at positions corresponding to one or more sites among the forehead, cheeks, and chin of the face to provide a warming function to large areas corresponding to one or more of the forehead, cheeks, and chin of the face.

Here, in the heating patch 100 for skin care according to an embodiment of the present disclosure, even when the heating part 130 is provided as a plurality of heating parts 130 and the plurality of heating parts 130 are connected in parallel to each other between the first electrode 121 and the second electrode 122, the plurality of heating parts 130 may be heated at the same temperature regardless of positions at which the heating parts 130 are formed.

Thus, in the heating patch 100 for skin care according to an embodiment of the present disclosure, uniform heat may be transferred from each heating part 130 toward the user's skin.

To this end, the plurality of heating parts 130 may be formed so that a total area of the plurality of conductive heating materials 133 included in each heating part 130 is the same. In this case, the plurality of conductive heating materials 133 included in a single heating part 130 may be formed to have the same area.

Also, the plurality of heating parts 130 may be formed so that a total length of the first heating electrode 131 and the second heating electrode 132 constituting each heating part 130 is the same, and a length of an overlapping area formed between the first heating electrode 131 and the second heating electrode 132 may be the same.

Here, in the plurality of heating parts 130, a distance between the first heating electrode 131 and the second heating electrode 132 facing each other in each heating part 130 may be the same.

As a preferred embodiment, the plurality of conductive heating materials 133 constituting a single heating part 130 may be formed to have the same area, and a total number and a total area of the plurality of conductive heating materials 133 included in each heating part 130 may be the same. Also, the overall length of each of the first heating electrode 131 and the second heating electrode 132, which constitute each heating part 130, may be formed to be the same, the first heating electrode 131 and the second heating electrode 132 may be disposed to be spaced apart at the same distance, and a length of an overlapping area formed between the first heating electrode 131 and the second heating electrode 132 may be the same.

In this way, in the heating patch 100 for skin care according to an embodiment of the present disclosure, a voltage of the same size may be supplied from the application electrode part 120 toward each heating part 130, and each heating part 130 may have the same self-resistance.

Accordingly, in the heating patch 100 for skin care according to an embodiment of the present disclosure, each conductive heating material 133 included in each heating part 130, as well as each heating part 130, may generate heat at a uniform temperature.

Thus, even when the heating patch 100 for skin care according to an embodiment of the present disclosure is implemented in the form of a sheet having a large heating area through the plurality of heating parts 130, each heating part 130 may generate heat at a uniform temperature.

In this way, even when the heating patch 100 for skin care according to an embodiment of the present disclosure is implemented as a sheet-type heating element through the plurality of heating parts 130, regardless of the overall shape and positions at which the heating parts 130 are formed, the heating temperature of each heating part 130 may be uniformly maintained throughout the entire area.

Meanwhile, the first electrode 121 and the second electrode 122 constituting the application electrode part 120 may be formed to have a relatively larger width than the first heating electrode 131 and the second heating electrode 132 constituting the heating part 130.

In this way, in the heating patch 100 for skin care according to an embodiment of the present disclosure, self-resistance of each of the first electrode 121 and the second electrode 122 may have a relatively smaller size than self-resistance of each of the first heating electrode 131 and the second heating electrode 132. Thus, power supplied from the outside may smoothly move toward the heating part 130 through the application electrode part 120.

A pair of cover members 140 may be disposed to surround the application electrode part 120 and the heating part 130 formed on at least one surface of the substrate part 110. In this way, the pair of cover members 140 may prevent external exposure of the application electrode part 120 and the heating part 130. Also, even when the heating patch 100 for skin care according to an embodiment of the present disclosure is applied to a wet environment, such as a sheet mask or a functional material applied to the user's body, the pair of cover members 140 may block introduction of a liquid material such as moisture into the application electrode part 120 and the heating part 130. Accordingly, the heating patch 100 for skin care according to an embodiment of the present disclosure may be stably driven even in the wet environment.

To this end, the pair of cover members 140 may be a plate-shaped sheet having a predetermined area to cover both the application electrode part 120 and the heating part 130.

The pair of cover members 140 may be made of a material such as a polymer resin, i.e., PU, polyethylene terephthalate (PET), polypropylene (PP), polyethylene (PE), or PVDF, release paper, fabric, or leather, may be made of a silicone material, or may be in the form of a molding that is covered with a resin material made of an insulator.

That is, the pair of cover members 140 may be made of a material having flexibility, and to allow the heating patch 100 for skin care according to an embodiment of the present disclosure to be applied to the wet environment, the pair of cover members 140 may be made of a material having moisture resistance in addition to flexibility and elasticity.

As a specific example, as illustrated in FIG. 2, the pair of cover members 140 may include a first cover member 141 and a second cover member 142 disposed on both surfaces of the substrate part 110, and the first cover member 141 and the second cover member 142 may be attached via an adhesive layer or fixed through heat fusion.

Here, the adhesive layer may be made of a liquid or gel inorganic material or a base material having an adhesive material applied to both surfaces thereof.

Also, the first cover member 141 may be a cover member that covers one surface of the substrate part 110 on which the conductive heating material 133 is formed, and the second cover member 142 may be a cover member that covers one surface of the substrate part 110 on which the conductive heating material 133 is not formed.

In this case, one surface of the first cover member 141 may be a contact surface that comes into contact with the user's skin.

Also, the first cover member 141 and the second cover member 142 may have a transparent color but may also have an opaque color such as black. In this case, the first cover member 141 and the second cover member 142 may have the same color or have different colors.

Here, the pair of cover members 140 may have a relatively greater hardness than the substrate part 110 while having flexibility.

For example, the pair of cover members 140 may be provided as thin film members and may be laminated on one surface of the substrate part 110.

In this way, even when the substrate part 110 is formed as a porous substrate, the pair of cover members 140 may support one surface of the substrate part 110 and provide a support force that allows the substrate part 110 to be unfolded. Accordingly, the pair of cover members 140 may reinforce the strength of the substrate part 110 and maintain the substrate part 110 in the shape of a plate.

Meanwhile, the pair of cover members 140 may include an exposing part 143 formed to be cut to allow a portion of the application electrode part 120 to be exposed to the outside. For example, the exposing part 143 may be formed in the pair of cover members 140 to allow an end portion of the first electrode 121 and an end portion of the second electrode 122 to be simultaneously exposed. In this way, the application electrode part 120 may be easily connected to an external power source through the exposing part 143. In this case, terminal sockets 123a and 123b having a predetermined length may be attached to the end portion of the first electrode 121 and the end portion of the second electrode 122, respectively, which are exposed to the outside through the exposing part 143.

Exemplary embodiments of the present disclosure have been described above, but the spirit of the present disclosure is not limited by the embodiments proposed herein. Those of ordinary skill in the art who understand the spirit of the present disclosure may easily propose other embodiments by addition, modification, omission, or the like of elements within the same spirit, but such changes also belong to the scope of the spirit of the present disclosure.

The invention claimed is:

1. A heating patch for skin care, the heating patch comprising:
 a substrate part;
 an application electrode part which is formed in a predetermined pattern on the substrate part and includes a first electrode and a second electrode, to which power from an external power source is applied;
 a heating part which includes a first heating electrode and a second heating electrode each extending a predetermined length from the first electrode and the second electrode, respectively, and facing each other at portions thereof without being electrically connected to each other, and includes a plurality of conductive heating materials which are formed to have a predetermined area in an overlapping portion where the first heating electrode and the second heating electrode face each other and which are configured to, when power is applied, generate heat while causing electricity to flow between the first heating electrode and the second heating electrode; and
 a pair of cover members disposed on both surfaces of the substrate part to prevent external exposure of the application electrode part and the heating part,
 wherein each of the first electrode and the second electrode comprises at least two layers including a first pattern disposed on the substrate part and a second pattern attached to the first pattern.

2. The heating patch of claim 1, wherein the first pattern is a printed pattern formed by filling pores in the substrate part with a conductive paste, and the second pattern is a metal sheet formed in the same shape as the first pattern.

3. The heating patch of claim 1, wherein the second pattern is attached to one surface of the first pattern via a conductive adhesive layer including a vertical conductive filler.

4. The heating patch of claim 1, wherein the first electrode is formed along an edge of the substrate part, and the second electrode is formed to be disposed on an inner side of the substrate part.

5. The heating patch of claim 1, wherein the first electrode includes a first portion and a second portion which are physically separated from each other so that the power from the external power source is able to be simultaneously applied along two paths, and the first portion and the second portion are formed on the substrate part so as to be, with respect to a virtual central line, disposed at both left and right sides of the central line.

6. The heating patch of claim 1, wherein the heating part is provided as a plurality of heating parts disposed between the first electrode and the second electrode, and the plurality of heating parts are connected in parallel to the application electrode part.

7. The heating patch of claim 6, wherein the plurality of heating parts are formed so that a total area of a conductive heating material included in each heating part is the same.

8. The heating patch of claim 6, wherein the plurality of heating parts are formed so that a total length of the first heating electrode and the second heating electrode included in each heating part is the same.

9. The heating patch of claim 1, wherein the first electrode and the second electrode are formed to have a relatively larger width than the first heating electrode and the second heating electrode.

10. The heating patch of claim 1, wherein the first heating electrode and the second heating electrode are a linear pattern bent one or more times.

11. The heating patch of claim 1, wherein the conductive heating material is a conductive constant-temperature heating material.

12. The heating patch of claim 1, wherein the cover member is made of a material that is moisture-proof and flexible.

13. The heating patch of claim 1, wherein the cover member is attached to one surface of the substrate part via an adhesive layer or is directly fixed to one surface of the substrate part through heat fusion.

14. The heating patch of claim 1, wherein the heating patch for skin care is in the form of a sheet mask that corresponds to a face.

15. The heating patch of claim 14, wherein, during use, the heating part is disposed at a position that corresponds to one or more sites among a forehead, cheeks, and a chin of the face.

16. The heating patch of claim 1, wherein the substrate part is a porous substrate having flexibility and elasticity.

* * * * *